United States Patent [19]
Branch et al.

[11] Patent Number: 5,114,984
[45] Date of Patent: May 19, 1992

[54] PROCESS FOR PRODUCING AN ANTIMICROBIALLY EFFECTIVE POLYURETHANE

[75] Inventors: Charles E. Branch, Norwalk; David F. Gavin, Cheshire; Thomas E. Robitaille, Portland, all of Conn.

[73] Assignee: Olin Corporation, Cheshire, Conn.

[21] Appl. No.: 692,331

[22] Filed: Apr. 26, 1991

[51] Int. Cl.$^5$ ............................................. C08G 18/14
[52] U.S. Cl. ................... 521/121; 106/18.33; 523/122; 524/718; 252/182.26
[58] Field of Search ............ 521/121; 106/18.33; 523/122; 524/718; 252/182.26

[56] References Cited

U.S. PATENT DOCUMENTS

| | | | |
|---|---|---|---|
| 2,809,971 | 10/1957 | Bernstein et al. | 260/270 |
| 3,636,213 | 1/1972 | Gerstein et al. | 424/245 |
| 3,940,482 | 2/1976 | Grand | 424/245 |
| 4,235,898 | 11/1980 | Watanabe et al. | 424/245 |
| 4,379,753 | 4/1983 | Bolich, Jr. | 252/106 |
| 4,401,770 | 8/1983 | Hance | 521/120 |
| 4,818,436 | 4/1989 | French et al. | 252/400.23 |
| 4,835,149 | 5/1989 | Burke et al. | 514/188 |
| 4,933,011 | 6/1990 | Rei | 106/18.31 |
| 4,935,061 | 6/1990 | French et al. | 106/170 |

OTHER PUBLICATIONS

Article from the Journal of the Society of Cosmetic Chemists entitled "Clear Zinc Pyrithione Preparations", presented May 24, 1971, Washington, D.C.

Primary Examiner—Maurice J. Welsh
Attorney, Agent, or Firm—Dale L. Carlson

[57] ABSTRACT

The present invention relates to a process for imparting anti-bacterial and anti-fungal properties to a polyurethane foam. Dissolving the pyrithione salt in an alkanolamine which is miscible with a polyol, makes this dissolved pyrithione an ideal candidate for use as a antimicrobial additive in this application. Prior use of pyrithiones in polyurethanes entailed using the powder form of zinc pyrithione. This was a dusty process as well as being difficult to disperse the pyrithione uniformly throughout the polyurethane foam. This invention overcomes both of these difficulties.

13 Claims, No Drawings

PROCESS FOR PRODUCING AN ANTIMICROBIALLY EFFECTIVE POLYURETHANE

FIELD OF THE INVENTION

This invention relates generally to a process for incorporating a difficult-to-solubilize biocide into a polyol and, more specifically, a method for solubilizing pyrithione in a polyol and the antimicrobially active polyurethane produced therewith.

BACKGROUND OF THE INVENTION

Pyrithione salts, such as zinc pyrithione, are known to provide excellent biocidal activity, including broad spectrum anti-bacterial and anti-fungal activity. There are many uses for these pyrithiones. By way of illustration, U.S. Pat. No. 4,818,436 discloses the use of pyrithiones in metal working fluids; U.S. Pat. No. 4,401,770 discloses urethane shoe inserts having antimicrobial activity; and U.S. Pat. No. 4,935,061 discloses their use in paints.

Unfortunately, these pyrithiones are solids, and the use of solids, such as powders, in the formulating and processing of polyurethane foams is undesireable for enviromental and safety reasons since the handling of a powder is generally a dusty process. Moreover, a powder is difficult to evenly disperse in a liquid polyol and is subject to settling problems, thus requiring stirring immediately before fabricating a urethane using the solids-containing polyol. Further, the pyrithione solids are difficult to solubilize, and interactions between prospective solvents and the polyols themselves are a particular concern.

Efforts have been made in the past to solubilize pyrithione salts for use in shampoos. For example, U.S. Pat. No. 3,636,213 discloses heavy metal pyrithione salts dissolved in an amine, preferably selected from the group consisting of dodecyl amine and diglycol amine, for use in hair dressings. As another illustration, U.S. Pat. No. 4,835,149 discloses the use of amines, including ethanolamine, diethanolamine, monoisopropylamine and others, together with a cosmetically effective amount of a polycarboxylic acid in the preparation of a shampoo effective for the treatment of seborrhea.

Heretofore, a solution to the problem of solubilizing pyrithione in a polyurethane forming formulation has not been known, to the knowledge of the present inventors. Such a solution would be highly desired by the polyurethanes manufacturing community.

SUMMARY OF THE INVENTION

In one aspect, the present invention relates to a process for producing an antimicrobially effective polyurethane which comprises the steps of:

(a) dissolving a pyrithione salt(s) in an alkanolamine to provide a dissolved pyrithione salt, (b) contacting said dissolved pyrithione salt with a polyol to provide a liquid mixture containing said polyol plus said dissolved pyrithione salt, and (c) reacting said liquid mixture with a polyisocyanate in order to produce a polyurethane characterized by uniform biocidal effectiveness throughout the polyurethane. In another aspect, steps (a) and (b) are carried out simultaneously, and in still another aspect, steps (a), (b) and (c) are carried out simultaneously.

In another aspect, the present invention relates to a polyurethane forming composition comprising:
(a) a polyol,
(b) a polyisocyanate,
(c) a biocidally effective amount of a solution consisting essentially of a pyrithione salt dissolved in an alkanolamine.

In still another aspect, the present invention relates to a polyol composition comprising:
(a) a polyol, and
(b) a biocidally effective amount of a solution consisting essentially of a pyrithione salt dissolved in an alkanolamine.

In yet another aspect, the present invention relates to the polyurethane produced by reacting the above polyurethane forming composition.

These and other aspects will become apparent upon reading the following detailed description of the invention.

DETAILED DESCRIPTION OF THE INVENTION

Pyrithione salts useful in the present invention include the zinc, magnesium, copper, and zirconium salts of pyrithione, and combinations thereof. The preferred pyrithione salt is zinc pyrithione. Zinc pyrithione is produced by reacting 1-hydroxy-2-pyridinethione or a soluble salt thereof with a zinc salt (eg.ZnSO4) to form a zinc pyrithione precipitate, as disclosed in U.S. Pat. No. 2,809,971.

The alkanolamine useful in the present invention preferably has less than six carbon atoms per molecule and more preferably is selected from the group consisting of monoisopropanolamine, monoethanolamine, and combinations thereof, most preferably monoisopropanolamine since this latter compound provides excellent miscibility in polyols.

The molar ratio of alkanolamine to pyrithione salt is preferably between about 0.5 and about 5, more preferably between about 0.5 and about 4.

The pyrithione salt is incorporated into the polyurethane forming formulation in an amount sufficient to provide biocidal effectiveness in the resulting polyurethane. "Biocidal effectiveness" is intended to designate that the polyurethane product (e.g., the foam, adhesive, elastomer, coating or sealant product) is inhibited against fungicidal or other microbial growth on, and within, the product. Utilizing the process of the present invention, the pyrithione salt, and its associated biocidal effectiveness, is uniformly distributed throughout the product. Preferably, between about 200 and about 2000, more preferably between about 500 and about 1200 ppm of pyrithione salt are employed based upon the weight of the polyurethane forming formulation.

The polyols which are used in the subject invention are well known in the art and are preferably those referred to as polyether polyols and/or polyester polyols or a combination thereof. The polyether polyols are prepared by the reaction of an alkylene oxide with polyhydric or polyamine-containing compounds, or mixtures thereof. Alkylene oxides which may be employed in the preparation of the polyols of the present invention include ethylene oxide, propylene oxide, butylene oxide, styrene oxide and the like. Halogenated alkylene oxides may also be used such as epichlorohydrin, 3,3,3-trichlorobutylene oxide, etc. Mixtures of any of the above alkylene oxides may also be employed. The preferred alkylene oxide is propylene oxide, or a mixture of propylene oxide with ethylene oxide.

Polyoxyalkylene polyether polyols are preferred and generally contain either primary or secondary hydroxyl groups, or mixtures thereof. These polyols are suitably prepared by reacting an active-hydrogen containing compound, such as polyhydric compounds or polyamines, with the above-described alkylene oxides. Useful polyhydric compounds include ethylene glycol, propylene glycol, diethylene glycol, dipropylene glycol, glycerol, pentaerythritol, sorbitol, sucrose, methyl glucoside, glucose, etc. Polyamine compounds which may be reacted with the alkylene oxide to prepare amine-based polyols include mono-, di-, and triethanolamine, ethylene diamine, diethylene diamine, toluene diamine, etc. These polyhydric alcohols and polyamine compounds can be reacted separately with alkylene oxides or they can be pre-mixed in the preparation of polyether polyol mixtures or blends. Preferred polyester polyols are those based on terephthalic, phthalic, isophthalic, adipic, succinic, glutanic, fumaric acid(s), and combinations thereof, and the like.

The polyol is employed in a proportion corresponding to between about 0.5 and about 1.2 equivalents per equivalent of polyisocyanate. Preferably, the polyol is employed in a proportion corresponding to between about 0.8 and about 1.0 equivalents per equivalent of polyisocyanate. Below the lower limit of about 0.5 equivalent of polyol per equivalent of polyisocyanate, the resulting foam is expected to be excessively friable. Above the upper limit of about 1.2 equivalents of polyol per equivalent of polyisocyanate, the resulting foam is expected to undergo excessive interior scorching and associated foam cell structure degradation during fabrication due to the increased exotherm of reaction by the additional polyol.

By "equivalents" of polyol is meant the molecular weight divided by the number of hydroxyl groups present in the molecule. The equivalent weight is expressed in whatever units, i.e., grams, pounds, tons, etc., are used to designate the amounts of the other components of the reaction mixture. Similarly, the term "equivalent" used in relation to the polyisocyanate has its usually accepted meaning, namely, the molecular weight of the polyisocyanate, in whatever units are used to designate the amounts of the various components of the reaction mixture, divided by the number of isocyanate groups present in the molecule.

The polyisocyanate employed in the present invention can be any of the polyisocyanates, organic and inorganic, known to be useful in the art of polymer formation. Such polyisocyanates are commonly employed in the preparation of polyurethanes by reaction with compounds containing two or more active hydrogen-containing groups.

Illustrative of such polyisocyanates are 2,4-tolylene diisocyanate, 2,6-tolylene diisocyanate, 4,4'-methylenebis(phenyl isocyanate), dianisidine diisocyanate, tolidine diisocyanate, hexamethylene diisocyanate, m-xylene diisocyanate 1,5-napthalene diisocyanate, p-phenylene diisocyanate 1,5-napthalene diisocyanate, p-phenylene diisocyanate, 1,4-diethylbenzene diisocyanate and the like. Mixtures of two or more of the above isocyanates can be used, such as mixtures of the 2,4- and 2,6-isomers of tolylene diisocyanate, mixture of the 2,4'- and 4,4'-isomers of methylenebis(phenyl isocyanate) and the like. In addition to the 4,4'-methylenebis (phenyl isocyanate) or mixtures of the 2,4'-isomer and 4,4'-isomer thereof which are employed as the isocyanate component, there can also be used modified forms of these isocyanates. For example, there can be used 4,4'-methylenebis(phenyl isocyanate), or an admixture thereof with a minor amount of the 2,4'-isomer, which has been treated to convert a minor proportion, generally less than 15 percent by weight of the starting material, to an artifact of said starting material. For example, the polyisocyanate component can be methylenebis(phenyl isocyanate) which has been converted to a stable liquid at temperatures of about 15° C. or higher.

Illustrative of another modified form of 4,4'-,methylenebis(phenyl isocyanate) which can form the polyisocyanate component is the product obtained by treating the former compound, or mixtures thereof with small Portions of 2,4'-isomer, with a minor portion of a carbodimide such as diphenylcarbodiimide. In accordance with said process, a minor proportion of the methylenebis(phenyl isocyanate) is converted to the corresponding isocyana-to-carbodiimide and there is obtained a mixture of a major proportion of unchanged starting material and a minor proportion of said isocyanato-substituted carbodimide.

Preferred as the polyisocyanate component is a mixture of methylenebis(phenyl isocyanate) with polymethylene polyphenyl isocyanates of higher functionality. Such mixtures are generally those obtained by phosgenation or corresponding mixtures of methylene bridged polyphenyl polyamines. The latter, in turn, are obtained by interaction of formaldehyde, hydrochloric acid and primary aromatic amines, for example, aniline, o-chloroaniline, o-toluidine and the like. Such polyamines, and polyisocyanates prepared therefrom, are known in the art. The preferred polyisocyanates are methylenebis(phenyl isocyanates) and the modified forms thereof including mixtures of polymethylene polyphenyl isocyanates containing from about 35 percent by weight to about 85 percent by weight of methylenebis(phenyl isocyanate). The most preferred polyisocyanate is a polymethylene polyphenyl isocyanate mixture containing from about 35 percent by weight to about 60 percent by weight of methylenebis(phenyl isocyanate), the remainder of said mixture being polymethylene polyphenyl isocyanates having a functionality greater than 2.0.

The amount of catalyst employed in the compositions of the present invention is a "catalytically effective" amount, i.e., an amount sufficient to catalyze the reaction of the polyisocyanate and the polyol to form polyurethane linkages. Advantageously, the catalyst is employed in an amount corresponding to no greater than about 10 weight percent based on the weight of the total composition. Preferably, the catalyst is a tertiary amine employed in a more preferred amount corresponding to between about 0.5 and about 5 weight percent based on the weight of the total composition, although tin catalysts such as dibutyltin dilaurate, or mixtures of amine and tin catalysts are also suitably employed. When using an amine-based polyol, the urethane-forming reaction can be sufficiently auto-catalytic so as to not require the incorporation of a separate catalyst. Indeed, it is preferred not to employ a catalyst with the amine-based polyols in order to minimize the possibility of scorch of the foam. However, when using other types of polyols to fabricate foams, a catalyst is generally preferred.

Useful tertiary amines are those which are generally employed to catalyze the reaction between an isocyanato group and an epoxide group. Such catalysts are a group of compounds well-recognized in the art of synthesizing polyurethanes.

Representative of said tertiary amine catalysts are: N,N-dialkylpiperazines such as N,N-dimethylpiperazine, N,N-diethylpiperazine and the like; trialkylamines such as trimethylamine, triethylamine, tributylamine and the like; 1,4-diazabicyclo(2-2-2)octane, which is more frequently referred to as triethylene diamine, and the lower-alkyl derivatives thereof such as 2-methyl triethylene diamine, 2,3-dimethyl triethylene diamine, 2,5-diethyl triethylene diamine and 2,6-diisopropyl triethylene diamine; N,N',N''-trialkylaminoalkylhexahydrotriazines such as N,N'N''-tris(dimethylaminomethyl) hexahydrotriazine, N,N',N''-tris(dimethylaminoethyl)-hexahydrotriazine, N,N',N''-tris(diethylaminopropyl)-hexahydrotriazine, N,N'N''-tris(diethylaminoethyl)hexahydrotriazine N,N'N''-tris(diethylaminopropyl) hexahydrotriazine and the like; mono-, di-, and tri-(dialkylaminoalkyl) monohydric phenols or thiophenols such as 2-(dimethylaminomethyl)phenol, 2-(dimethylaminobutyl)phenol, 2-(diethylaminoethyl)phenol, 2-(diethylaminobutyl)phenol, 2-(dimethylaminomethyl)thiophenol, 2-(diethylaminoethyl)thiophenol, 2,4-bis(dimethylaminoethyl)phenol, 2,4-bis(dipropylaminobutyl)phenol, 2,4-bis(dipropylaminoethyl)-phenol, 2,4-bis(dimethylaminoethyl)thiophenol, 2,4-bis(diethylaminopropyl)triophenol, 2,4-bis(dipropylaminoethyl)-thiophenol, 2,4,6-tris(dimethylaminoethyl)-phenol, 2,4,6-tris(diethylaminoethyl)-phenol, 2,4,6-tris(dipropylaminomethyl) phenol, 2,4,6-tris(diethylaminoethyl)thiophenol, 2,4,6-tris(dimethylaminoethyl) thiophenol and the like; N, N, N'N'-tetraalkylalkylenediamines such as N,N,N',N'-tetramethyl-1,3-propane diamine, N,N,N',N'-tetramethyl-1,3-butanediamine, N,N,N',N'-tetramethylethylenediamine and the like; N,N-dialkylcyclohexylamines such as N,N-dimethylcyclohexylamine, N,N-diethylcyclohexylamine and the like; N-alkylmorpholines such as N-methylmorpholine, N-ethylmorpholine and the like; N,N-dialkylalkanolamines such as N,N-dimethylethanolamine, N,N-diethylethanolamine and the like; N,N,N',N'-tetraalkylguanidines such as N,N,N',N'-tetramethylguanidine, N,N,N',N'-tetraethylguanidine and the like. Also useful are acid-blocked tertiary amine catalysts, where the blocking agent is, for example, 2-ethylhexanoic acid. The preferred tertiary amine catalysts are dimethylethanolamine (DMEA) and POLY-CAT-8(a product of Abbott Corp.), N,N-dimethylcyclohexyl amine.

If desired, any organometallic compound known to be a catalyst in the reaction between an isocyanato group and an active hydrogen-containing group can be employed in the compositions of the present invention. Such catalysts include the organic acid salts of, and the organometallic derivatives of, bismuth, lead, tin, iron, antimony, uranium, cadmium, cobalt, thorium, aluminum, mercury, zinc, nickel, cerium, molybdenum, vanadium, copper, manganese, and zirconium. The preferred group of said organometallic derivatives is that derived from tin. Examples of this preferred group are: dibutyltin diacetate, dibutyltin dilaurate, stannous octoate, stannous oleate, and the like.

If a polyurethane foam product is desired, suitable blowing agent(s) are employed in order to achieve the blowing of the foam. Suitable blowing agents include halocarbons, such as monochlorodifluoromethane, or non-halocarbons such as water which produces blowing by virtue of carbon dioxide production during the polyurethane forming reaction. Generally speaking, the amount of blowing agent employed depends upon the desired density. Thus, if low density foams, i.e., 1.0 to 6 pounds per cubic foot, are desired, the amount of the halogenated-hydrocarbon blowing agent, if used, is between about 5 and about 25 percent by weight based on the total weight of the foam formulation.

Optional additives such as dispersing agents, cell stabilizers, surfactants, flame retardants, and the like, which are commonly employed in the fabrication of polymer foams, can be employed in the process of the invention. For example, the well-known phosphorus-based flame retardant additives may be used if flame retardancy is desired. These phosphate additives generally do not adversely affect the physical properties of the foam even if they are hydrolyzed and/or physically removed from the foam since these additives are not part of the foam backbone. As another illustration, a finer cell structure may be obtained if organosilicone polymers are used as surfactants in the reaction mix.

Other optional additives, such as inorganic and organic fillers, can be employed in the process of this invention. Illustrative inorganic fillers are calcium carbonate, silica, glass, antimony oxides, etc. Illustrative organic fillers are the various polymers, copolymers of vinyl chloride, vinyl acetate, acrylonitrile, styrene, melamine, partially oxyalkylated melamine, etc. Organic esters can also be employed if desired. Particularly preferred esters are those derived from dicarboxylic acids such as oxalic, malonic, succinic, glutaric, maleic, phthalic, isophthalic and terephthalic acids. The use of an organic filler, particularly isophthalic and/or terephthalic esters, is preferred in the composition of the present invention since these organic fillers are liquid and soluble in the "B-side".

It is preferred in preparing the polyurethane foams of the invention to include in the foam forming reaction mixture a small proportion of a conventional surfactant in order to improve the cell structure of the resulting foam. Typical such surfactants are the silicones and the siloxaneoxyalkylene block copolymers. If used, generally between about 0.2 and about 5 parts by weight of surfactant are employed per hundred parts of polyol.

The polyurethanes treated in accordance with the process of the present invention inhibit the growth of Gram (+) and Gram (−) bacteria, yeast and fungi, including pathogenic disease causing microorganisms which are of particular interest in hospital an other institutional environments.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

The following examples are intended to illustrate, but in no way limit the scope of, the present invention.

EXAMPLE 1

Antimicrobial Testing of Urethane Foam Containing Zinc Pyrithione Dissolved in Monoethanolamine A zinc pyrithione powder, commercially available as zinc OMADINE ® powder, a product of Olin Corporation, was dissolved in ethanolamine to 42% active ingredient (w/w). This solution was then diluted to 5% zinc pyrithione with Poly-G 20-56, an Olin Corporation trifunctional poly ether polyol. This mixture was then added to a typical urethane foam formulation as described below. A standard ASTM G21-85 fungal challenge was then conducted on the resulting foam as well as a control blank. Each sample was run in duplicate, reported below.

| Formulation | |
|---|---|
| Ingredients | Parts by Weight |
| Polyol[1] | 100 |
| Water | 5 |
| Surfactant[2] | 1.0 |
| Tertiary Amine[3] | 0.25 |
| Stannous Octoate (50% solution in dioctyl phthalte)[4] | 0.75 |
| Toluene diisocyanate[5] | 94.1 |
| Dissolved zinc pyrithione solution[6] | 1.0 |

[1] POLY-G 20-56, a poly ether triol having a molecular weight of 3000 and a hydroxyl number of 56, a product of Olin Corporation
[2] Silicone surfactant sold under the name DC-5125, of Air Products
[3] A tertiary Amine sold under the name of 33LV, of Air Products
[4] A stannous octoate sold under the name T-10, of Air Products
[5] A mixture of toluene diisocyanate isomers (80:20 mixture of 2,4/2,6 isomers), product of Olin Corporation The ASTM G21-85 Fungal Challenge is the standard test procedure to determine Fungal resistance of a polymeric material. This consists of placing a two inch disc of the polymr on a nutrient salt agar and spraying the polymer with a fungal spore suspension of the following fungi:

| | |
|---|---|
| Aspergillus niger | ATCC 9642 |
| Penicillium funiculosum | ATCC 9644 |
| Chaetomium globosum | ATCC 6205 |
| Gliocladium virens | ATCC 9645 |
| Aureobasidium pullulans | ATCC 9348 |

This is then incubated at 32° C. for a minimum of three weeks and rated as to the amount of growth on the polymer surface as described below:

| ASTM G21 Fungal Challenge Results | | | | |
|---|---|---|---|---|
| Test Sample | Week 1 | Week 2 | Week 3 | Week 4 | Week 5 |
| Treated Sample | 0,0 | 0,0 | 0,0 | 0,0 | 0,0 |
| Untreated Sample | 0,1 | 1,1 | 1,2 | 1,2 | 1,2 |

0 = No fungal growth observed
1 = Up to 10% fungal growth observed on polymer surface
2 = >10 to 30% fungal growth observed on polymer surface

EXAMPLE 2

Antimicrobial Testing of Urethane Foam Containing Zinc Pyrithione Dissolved in Monoisopropanolamine Commercially available zinc OMADINE ® powder, a product of Olin Corporation was dissolved in monoisopropanolamine to 15% (w/w) active level. This solution was then diluted to 2% with POLY G ® 20-56, a trifunctional polyether polyol product of Olin Corporation. A polyurethane foam was then formed by typical foaming techniques. This foam was made as described in Example 1.

A Zone of Inhibition test was performed on discs of the resulting foam. Zone of inhibition test is a standard test for microbiologicals and may be applied to fungi as well. This test measures the zone of inhibited microbial growth surrounding a sample. In this procedure two inch discs of the urethane foam are placed in a petri dish, on a nutrient containing agar and inoculated with a suspension of bacteria or fungi. These foam discs are incubated for 48 hours at 32° Celsius. Antimicrobial activity is evaluated by observing an area of no growth around the foam disc as well as the foam's contact area with the agar. An area of no growth around the swatch is known as a zone of inhibition. An untreated sample should not produce a zone of inhibition.

Zones were observed against all microbes tested including *Staphylococcus aureus*—Gram (+) bacteria, and *Klebsiella pneumoniae*—Gram (−) bacteria in the treated foam. Bacteria strains used in this test are recommended test organisms in the AOAC method "Bacteriostatic Activity of Laundry Additive Disinfectants", 1984.

Having thus described the invention, what is claimed is:

1. A process for producing an antimicrobially effective polyurethane which comprises the steps of:
    (a) dissolving a pyrithione salt(s) in an alkanolamine to provide a dissolved pyrithione salt,
    (b) contacting said dissolved pyrithione salt with a polyol to provide a liquid mixture containing said polyol plus said dissolved pyrithione salt, and
    (c) reacting said liquid mixture with a polyisocyanate in order to produce a polyurethane characterized by uniform biocidal effectiveness throughout the polyurethane.

2. The process of claim 1 wherein steps (a) and (b) are carried out simultaneously.

3. The process of claim 1 wherein steps (a), (b) and (c) are carried out simultaneously.

4. The process of claim 1 wherein said pyrithione salt is selected from the group consisting of the zinc, magnesium, copper, and zirconium salts of pyrithione, and combinations thereof.

5. The process of claim 1 wherein said alkanolamine is selected from the group consisting of monoisopropanolamine, monoethanolamine, and combinations 6. A polyurethane forming composition comprising:
    (a) a polyol,
    (b) a polyisocyanate,
    (c) a biocidally effective amount of a solution consisting essentially of a pyrithione salt dissolved in an alkanolamine.

7. The composition of claim 6 wherein said pyrithione salt is selected from the group consisting of the zinc, magnesium, copper, and zirconium salts of pyrithione, and combinations thereof.

8. The composition of claim 6 wherein said alkanolamine is selected from the group consisting of monoisopropanolamine, monoethanolamine, and combinations thereof.

9. The composition of claim 6 wherein said pyrithione salt is present in an amount of between about 200 and about 2000 ppm of pyrithione salt based upon the weight of the composition.

10. A polyol composition comprising:
    (a) a polyol, and (b) a biocidally effective amount of a solution consisting essentially of a pyrithione salt dissolved in an alkanolamine.

11. The composition of claim 10 wherein said pyrithione salt is selected from the group consisting of the zinc, magnesium, copper, and zirconium salts of pyrithione, and combinations thereof.

12. The composition of claim 10 wherein said alkanol amine is selected from the group consisting of monoisopropanolamine, monoethanolamine, and combinations thereof.

13. The composition of claim 10 wherein the molar ratio of alkanolamine to pyrithione salt is between about 0.5 and about 5.

* * * * *